US00PP24825P3

(12) United States Plant Patent

Klemm et al.

(10) Patent No.: US PP24,825 P3

(45) Date of Patent: Aug. 26, 2014

(54) *CALIBRACHOA* PLANT NAMED 'KLECA12224'

(50) Latin Name: ***Calibrachoa* sp.**
Varietal Denomination: KLECA12224

(71) Applicant: Klemm+Sohn GmbH & Co. KG, Stuttgart (DE)

(72) Inventors: Nils Klemm, Stuttgart (DE); Anita Stöver, Ostfildern (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 93 days.

(21) Appl. No.: 13/694,206

(22) Filed: Nov. 7, 2012

(65) Prior Publication Data

US 2014/0130223 P1 May 8, 2014

(51) Int. Cl.
*A01H 5/00* (2006.01)

(52) U.S. Cl.
USPC ..... Plt./413

(58) Field of Classification Search
USPC ..... Plt./413
See application file for complete search history.

*Primary Examiner* — Kent L Bell

(74) *Attorney, Agent, or Firm* — Jondle Plant Sciences Division of Swanson & Bratschun, L.L.C.

(57) ABSTRACT

A new and distinct variety of *calibrachoa* plant named 'KLECA12224' particularly distinguished by yellow flowers and very early flowering is disclosed.

1 Drawing Sheet

Genus and species: *Calibrachoa* sp.
Variety denomination: 'KLECA12224'.

BACKGROUND OF THE NEW PLANT

The present invention comprises a new and distinct variety of *calibrachoa*, botanically known as *Calibrachoa* sp. and hereinafter referred to by the variety name 'KLECA12224'. The new variety was the result of a controlled cross conducted in May 2008 in Stuttgart, Germany, between the female parent *calibrachoa* plant 'KLECA07153' (U.S. Plant Pat. No. 19,881), and the male parent *calibrachoa* plant 'CA080159' (unpatented). A single plant selection was subsequently chosen for further evaluation and asexual propagation.

The new variety was first propagated by vegetative cuttings and in vitro propagation in May 2009 in Stuttgart, Germany and has been asexually reproduced repeatedly by vegetative cuttings for more than 70 generations. The present invention has been found to retain its distinctive characteristics through successive asexual propagations via vegetative cuttings.

Plant Breeder's Rights for 'KLECA12224' were applied for in Canada on Feb. 6, 2012. 'KLECA12224' has not been made publicly available or sold anywhere in the world more than one year prior to the filing date of this application.

SUMMARY OF THE INVENTION

The following are the most outstanding and distinguishing characteristics of this new variety when grown under normal horticultural practices in a glass greenhouse in Stuttgart, Germany.

1. Yellow flowers; and
2. Very early flowering.

DESCRIPTION OF THE PHOTOGRAPH

This new *calibrachoa* plant is illustrated by the accompanying photograph which shows inflorescences and foliage of the plant. The colors shown are as true as can be reasonably obtained by conventional photographic procedures. The photograph was taken in May 2012 of a 5-month old *calibrachoa* plant grown in an 11 centimeter pot in a glass greenhouse in Stuttgart, Germany under normal horticultural practices.

DESCRIPTION OF THE NEW VARIETY

The following detailed descriptions set forth the distinctive characteristics of 'KLECA12224'. The data which defines these characteristics were collected from asexual reproductions carried out in Stuttgart, Germany. The plant history was taken in May 2012 of 5-month old plants grown in 11 centimeter pots in a glass greenhouse. Plants were pinched once after potting. Color readings were taken under natural light at an illumination of approximately 20 Klx. Color references are primarily to The R.H.S. Colour Chart of The Royal Horticultural Society of London (R.H.S.), Fifth Edition (2007).

DETAILED BOTANICAL DESCRIPTION OF THE NEW PLANT

Classification:
- *Family*.—Solanaceae.
- *Botanical*.—*Calibrachoa* sp.
- *Common*.—*Calibrachoa*.
- *Denomination*.—'KLECA12224'.

Parentage:
- *Female*.—*Calibrachoa* plant 'KLECA07153' (U.S. Plant Pat. No. 19,881).
- *Male*.—*Calibrachoa* plant 'CA080159' (unpatented).

Growth:
- *Form*.—Uniformly mounded.
- *Habit*.—Upright to cascading.
- *Height* (*measured from the top of the soil*).—16.0 cm.
- *Width* (*horizontal plant diameter*).—14.0 cm.
- *Time to produce a finished flowering plant*.—6 weeks after potting.

*Outdoor plant performance*.—Continuous flowering.
*Time to initiate and develop roots*.—22 days.
*Root description*.—Fine, fibrous, freely branching, moderate density.
*Root color*.—RHS 155C.

Stems:
*Length of basal branches*.—8.0 cm.
*Internode length*.—1.5 cm.
*Stem diameter*.—0.3 cm.
*Diameter of branches* (*from midpoint*).—7.0 cm.
*Stem color*.—RHS 142A.
*Texture*.—Smooth.
*Anthocyanin*.—Absent.
*Pedicel*.—Color: RHS 142B. Length: 3.5 cm. Diameter: 0.2 cm. Texture: Smooth.
*Peduncle*.—Color: RHS 144A. Length: 1.9 cm. Diameter: 0.1 cm.

Leaves:
*Arrangement*.—Alternate, simple, sessile.
*Length*.—3.5 cm.
*Width*.—1.0 cm.
*Shape*.—Lanceolate to elliptic.
*Apex*.—Obtuse to slightly acute.
*Base*.—Attenuate.
*Margin*.—Entire.
*Color* (*immature leaves*).—Upper surface: RHS 147B. Lower surface: RHS 137D.
*Color* (*mature leaves*).—Upper surface: RHS 147A. Lower surface: RHS 137D.
*Texture* (*both surfaces*).—Smooth.
*Venation pattern*.—Pinnate.
*Venation color*.—RHS 145A.
*Petioles*.—Absent.

Flower bud:
*Shape*.—Irregular to oblong.
*Length*.—1.4 cm.
*Diameter*.—0.4 cm.
*Color at tight bud*.—RHS 1B.

Inflorescence:
*Blooming habit*.—Flowers face upright, axillary.
*Inflorescence type*.—Single flower, determinate inflorescence.
*Lastingness of individual blooms on the plant*.—5 days.
*Fragrance*.—Absent.

Flowers:
*Immature flower*.—Width: 2.5 cm. Length: 2.0 cm. Depth: 1.8 cm. Color: Upper surface: RHS 7A. Lower surface: RHS 8A.
*Mature flower*.—Width: 3.0 cm. Length: 2.0 cm. Depth: 2.0 cm. Color: Upper surface: RHS 9A. Lower surface: RHS 10A.
*Corolla tube*.—Color inside: RHS 12A. Color outside: RHS 10A. Tube length: 1.7 cm. Tube diameter: 0.9 cm. Throat diameter: 0.8 cm. Texture (inside & outside): Smooth.
*Petals*.—Length: 1.3 cm. Width: 1.7 cm. Shape: Heart-shaped. Apex: Obverse. Base: Open and fused into the tube. Margin: Entire. Waviness of petals: Very weak. Lobation: Weak. Texture (both surfaces): Smooth.
*Sepals*.—Calyx (composition): Actinomorphic. Shape: Lanceolate to elliptic. Apex: Acute. Base: Open and tube is fused into the base. Margin: Entire. Length: 1.4 cm. Width: 0.2 cm. Color: Upper surface: RHS 143B. Lower surface: RHS 143C. Texture (both surfaces): Smooth.

Reproductive organs:
*Stamens*.—Quantity: 5. Filament color: RHS 151C. Filament length: 0.8 cm. Filament diameter: 0.1 cm. Anther color: RHS 6A. Pollen color: RHS 13B. Pollen quantity: Sparse.
*Pistils*.—Quantity: 1. Length: 0.7 cm. Diameter: 0.1 cm. Stigma color: RHS 150A. Style color: RHS 150A.

Fruit and seed set: No fruit or seed set observed.

Disease and insect resistance: No particular resistance to disease or pests observed.

COMPARISON WITH PARENTAL AND COMMERCIAL VARIETIES

'KLECA12224' differs from the female parent *calibrachoa* plant 'KLECA07153', (U.S. Plant Pat. No. 19,881) in that 'KLECA12224' has yellow colored flowers, whereas 'KLECA07153' has red colored flowers.

'KLECA12224' differs from the male parent *calibrachoa* plant 'CA080159' (unpatented) in that 'KLECA12224' has yellow colored flowers, whereas 'CA080159' has orange colored flowers.

'KLECA12224' differs from the commercial cultivar, 'MiniFamous Compact Yellow' (unpatented), in that 'KLECA12224' has yellow colored flowers, whereas 'MiniFamous Compact Yellow' has lighter yellow colored flowers.

We claim:

1. A new and distinct variety of *calibrachoa* plant named 'KLECA12224' as shown and described herein.

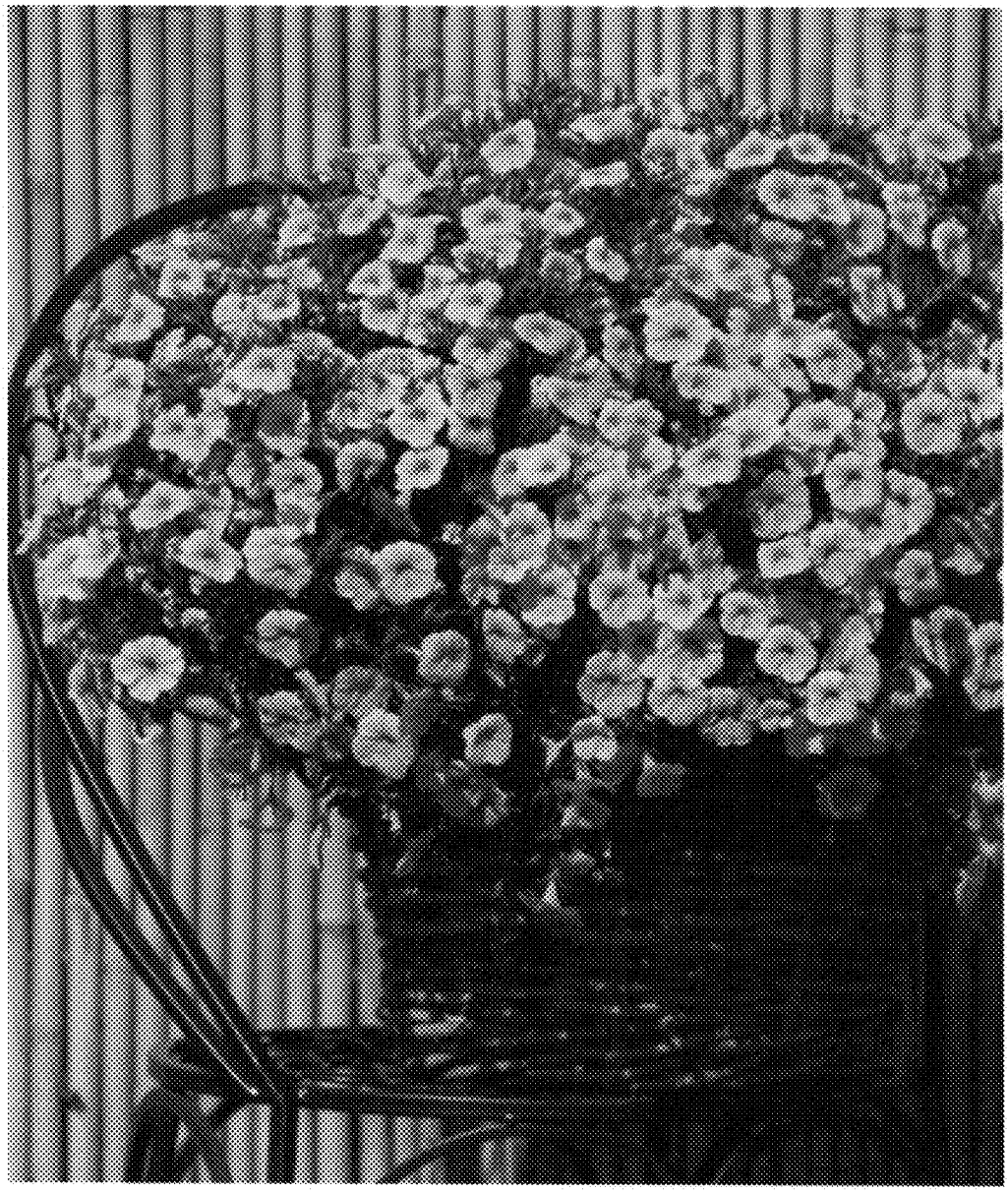

* * * * *